United States Patent [19]

Schäfer et al.

[11] 4,045,295
[45] Aug. 30, 1977

[54] PURIFICATION OF SULFURIC ACID CONTAINING ACETIC ACID

[75] Inventors: Stefan Schäfer, Bruhl; Alexander Ohorodnik, Erftstadt-Liblar; Klaus Gehrmann, Erftstadt-Lechenich; Albert Mainski, Rodenkirchen, all of Germany

[73] Assignee: Hoechst Aktiengesellschaft, Frankfurt am Main, Germany

[21] Appl. No.: 694,664

[22] Filed: June 10, 1976

[30] Foreign Application Priority Data

June 12, 1975 Germany .............................. 2526241

[51] Int. Cl.$^2$ ............................ B01D 3/10; B01D 3/34
[52] U.S. Cl. ........................................ 203/79; 203/80; 203/85; 203/92; 203/95; 423/531
[58] Field of Search ...................... 203/73, 74, 77, 81, 203/91, 79, 80, 85, 92, 96, 95; 423/531, 488; 260/703, 541

[56] References Cited

U.S. PATENT DOCUMENTS 3,635,664   1/1972   Morimoto .................. 423/488

FOREIGN PATENT DOCUMENTS 2,027,018   3/1971   Germany .................. 423/488
320,447   1/1972   U.S.S.R. .................. 423/488

Primary Examiner—Hiram H. Bernstein
Attorney, Agent, or Firm—Connolly and Hutz

[57] ABSTRACT

Dilute sulfuric acid contaminated with acetic acid and hydrogen chloride is purified with the resultant formation of concentrated sulfuric acid and acetic acid. To this end, the contaminated sulfuric acid is heated in a first step to at most 60° C under 25–30 mm Hg so as to expel all of the hydrogen chloride together with minor proportions of acetic acid and water. In a second step, the sulfuric acid is heated to at most 165° C under 20–25 mm Hg so as to distil off the bulk of acetic acid together with water. In a third step, the sulfuric acid is cooled down to 60°–90° C, diluted with 10–30 wieght % of water with agitation and while cooling is continued. Following this, the sulfuric acid is heated to 160°–165° C under 20–25 mm Hg and thereby freed from the water and residual acetic acid.

6 Claims, 1 Drawing Figure

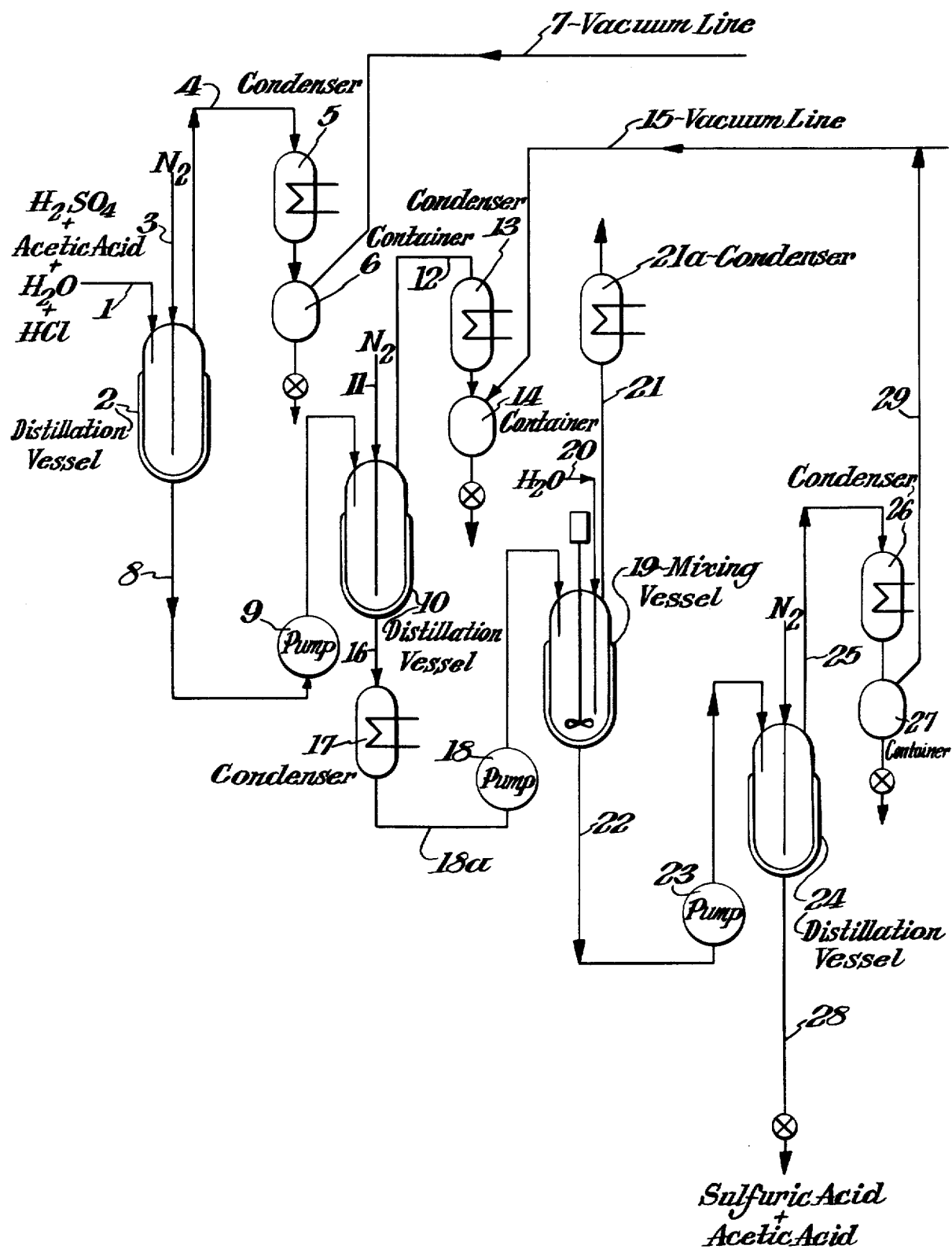

PURIFICATION OF SULFURIC ACID CONTAINING ACETIC ACID

The present invention relates to the purification of sulfuric acid containing acetic acid, such as that which is obtained as a by-product in the purification of crude hydrogen chloride described in U.S. Pat. No. 4,003,723.

U.S. Pat. No. 4,003,723 describes a process for the purification of a crude hydrogen chloride gas by-product, which is obtained in the production of chloroacetic acids by the catalytic chlorination of acetic acid with chlorine gas in contact with acetic anhydride and/or acetyl chloride, and continues to be contaminated, even after having been prepurified, with about 0.6 up to 3 % by volume of acetyl chloride and optionally with some minor proportion of chloroacetyl chloride, which process comprises: introducing the crude hydrogen chloride gas into the base portion of a scrubbing zone and scrubbing it countercurrently therein with about 0.5 up to 20 liter, per normal cubic meter (S.T.P) of hydrogen chloride gas, of a cooled scrubbing liquid kept under circulation and consisting substantially of about 20 up to 80 weight % of concentrated $H_2SO_4$, about 15 up to 60 weight % of acetic acid, and about 5 up to 50 weight % of water; introducing the resulting purified moist hydrogen chloride gas issuing at the head of the scrubbing zone into the base portion of a drying zone and drying it therein by scrubbing it countercurrently with precooled sulfuric acid kept under circulation, the sulfuric acid being used at a rate of about 0.5 up to 20 liter, per normal cubic meter of hydrogen chloride; and removing dry hydrogen chloride near the head of the drying zone.

Upon partial replacement of the scrubbing liquid under circulation in the scrubbing column, it is necessary for an adequate proportion (adequate with respect to the quantity of dilute sulfuric acid supplied) of scrubbing liquid contaminated with acetic acid to be taken from the cycle. This, however, is a mixture which admits of no technical uses and which cannot be discarded for reasons of ecology. In view of this, it is highly desirable to have a process permitting the mixture to be separated into sulfuric acid and acetic acid, respectively, for further use of these two materials.

It has been described that dilute sulfuric acid can be transformed to more concentrated sulfuric acid by heating. Concentrated sulfuric acid is known for its dehydrating and oxidizing power so that it is necessary for the sulfuric acid used in this process to be free from organic compounds as these would be destroyed on concentrating the acid.

As described in German patent specification No. 1,124,024, it is possible for dilute sulfuric acid to be freed from minor proportions of organic and inorganic contaminants by a process, which provides for the sulfuric acid to be treated with a minor quantity of hydrogen sulfide, generally with about 5 up to 50 mg per liter of sulfuric acid, in the presence of active carbon, for the active carbon to be subsequently separated from sulfuric acid, and for residual hydrogen sulfide to be destroyed by treatment with hydrogen peroxide in the presence of active carbon. This process which relates to the treatment of slightly contaminated sulfuric acid does not provide for the contaminants to be recovered and is accordingly not applicable to the problem underlying the present invention.

We have now unexpectedly found that it is possible for acetic acid to be separated from a mixture with sulfuric acid by distillative treatment under specific conditions which substantially avoid partial decomposition of the mixture.

The present invention thus provides a process for purifying dilute sulfuric acid contaminated with acetic acid and hydrogen chloride with the resultant formation of concentrated sulfuric acid of about 94–96 % strength and acetic acid, the sulfuric acid to be purified forming part of a mixture consisting substantially of about 30–60 weight % of concentrated sulfuric acid, about 20–50 weight % of acetic acid, about 10–40 weight % of water, and about 2–10 weight % of hydrogen chloride, which process comprises: heating, in a first step, the contaminated sulfuric acid to a temperature of at most about 60° C under a pressure of about 25–30 mm Hg and thereby expelling all of the hydrogen chloride together with minor proportions of acetic acid and water; heating, in a second step, the sulfuric acid to a temperature of at most 165° C under a pressure of about 20–25 mm Hg and thereby distilling off the bulk of acetic acid together with water with the resultant formation of (a) sulfuric acid containing at most 1.3 up to 1.6 weight % of residual acetic acid and (b) of acetic acid of about 70–80 weight % strength; cooling, in a third step, the sulfuric acid down to a temperature of about 60°–90° C, diluting it with about 10–30 weight % of water with agitation and while cooling is continued, and then heating the sulfuric acid to a temperature of about 160°–165° C under a pressure of about 20–25 mm Hg and thereby freeing it from the water and residual acetic acid.

A preferred feature of the present process provides for the sulfuric acid to be heated in the first step to 55° up to 60° C and in the second step to 163° up to 165° C. It is also advantageous, in the second step, to remove all acetic acid, with the exception of about 1.5 weight %, from the sulfuric acid. It is equally preferable in the third step to cool the sulfuric acid down to a temperature of about 70° C and then mix it with a certain quantity of water. It is finally preferable for last residual proportions of acetic acid to be removed from the sulfuric acid by heating the latter to 165° C under 20 mm Hg.

The sulfuric acid purified in the manner just described contains about 4 up to 6 weight % of water and less than 0.05 weight % of acetic acid. It is a colorless liquid which is suitable for use as a scrubbing liquid in the process described in U.S. Pat. No. 4,003,723, and can practically be used as often as desired, once it is has been regenerated by the process of the present invention. Sulfuric acid which was regenerated 15 times underwent a slight discoloration which disappeared after the addition of some hydrogen peroxide.

The process of the present invention may be effected batchwise or continuously. If carried out continuously, the sulfuric acid containing acetic acid should preferably be introduced continuously into a first distilling zone operated at a base temperature of 60° C and under a pressure of 25–30 mm Hg, the volatile fractions should be removed overhead, and a quantity of sulfuric acid corresponding to that supplied should be removed from the base portion of the distilling zone and introduced into a second distilling zone, which should be operated at 165° C under a pressure of 20 mm Hg, wherein the bulk quantity of acetic acid having a strength of about 80 % and being free from hydrogen chloride is obtained as the distillate. A quantity of base product corresponding to the quantity of sulfuric acid supplied is continuously taken from the base portion of the second distilling column, the base product is cooled down to about 70° C, mixed with a certain quantity of water and the resulting mixture is introduced into a third distilling zone, which is operated at a base temperature of 165° C and under a pressure of 20 mm Hg and in which a 3-5 weight % aqueous acetic acid solution is obtained as the distillate and purified sulfuric acid is obtained as the base product.

Describing the invention with reference to the drawing: 18.5 kg of a mixture consisting of 47 weight % of $H_2SO_4$, 28 weight % of acetic acid, 21 weight % of water, and 4 weight % of HCl was continuously introduced through line 1 into heatable distilling vessel 2, gradually heated therein to 60° C under a pressure of 25 to 30 mm Hg, which was produced by means of vacuum pipe 7, and distilled (process step 1). The distillate removed near the head of distilling vessel 2 and line 4 was condensed in condenser 5 and the condensate was collected in container 6. The distillate was 1.6 kg of aqueous acetic acid of 83.8 weight % strength. The distillate also contained all the hydrogen chloride initially present in the starting mixture. Base product accumulating in the base of distilling vessel 2, was removed through line 8 in a quantity corresponding to the quantity of starting mixture supplied, delivered by means of pump 9 to distilling vessel 10 and distilled therein at 165° C under 20 mm Hg (process step 2). The distilled fraction removed near the head of distilling vessel 10 and line 12 was condensed in condenser 13 and the condensate was collected in container 14. 4.88 kg of the distilled fraction containing acetic acid and water in a ratio by weight of 70 : 30, was obtained together with 2.25 kg of last runnings consisting of acetic acid of 16 weight % strength. Distilling vessel 10 was maintained under vacuum which was produced by means of vacuum pipe 15. The base product obtained in distilling vessel 10 consisted of hot sulfuric acid with 1.4 weight % of acetic acid. It was removed through line 16, cooled down to about 70° C in condenser 17, and delivered by means of pump 18 and through conduit 18 a to mixing vessel 19 (process step 3). In mixing vessel 19, the sulfuric acid was diluted with agitation with 3.4 kg of water, which came from line 20. The mixing vessel was deaerated through line 21 and condenser 21 a. The dilute sulfuric acid was delivered by means of pump 23 through line 22 to distilling vessel 24 and distilled at 165° C under 20 mm Hg. The distillate coming from distilling vessel 24 was conveyed through line 25 to condenser 26, condensed, and the condensate was collected in container 27. The distillate was 3.52 kg of water containing 3.5 weight % of acetic acid. Distilling vessel 27 was connected by means of line 29 to vacuum pipe 15. The distillation residue obtained in distilling vessel 24 was colorless sulfuric acid of 95 weight % strength, which contained 0.05 weight % of acetic acid. It was removed through line 28.

The process of the present invention has technically beneficial effects inasmuch as it enables sulfuric acid, which is contaminated with acetic acid, to be regenerated and the two acids to be purified so that it is possible for them to be put to further commercial uses.

EXAMPLE 18.5 kg of a mixture consisting of 47 weight % of sulfuric acid, 28 weight % of acetic acid, 21 weight % of water and 4 weight % of HCl was introduced into a heatable distilling vessel, gradually heated therein to 60° C under a pressure of 25-30 mm Hg and distilled. 1.6 kg of a 83.8 weight % aqueous acetic acid was obtained as the distillate which also contained all of the hydrogen chloride initially present in the mixture. Following this, the temperature in the distilling vessel was gradually increased to 165° C under a constant pressure of 20 mm Hg. 4.88 kg of a distillate fraction consisting of acetic acid and water in a ratio by weight 70:30 and 2.25 kg of a 16 weight % acetic acid (last runnings) were obtained under these conditions. The hot sulfuric acid which still contained 1.4 weight % of acetic acid was cooled down to 70° C and mixed with 3.4 kg of water with agitation and while cooling was continued. To remove residual acetic acid, the cooled mixture was heated to 165° C under a pressure of 20 mm Hg, whereby 3.52 kg of steam containing 3.5 weight % of acetic acid was expelled and condensed. The colorless distillation residue consisted of a 95 weight % sulfuric acid which still contained 0.05 weight % of acetic acid.

We claim:

1. A process for purifying dilute sulfuric acid contaminated with acetic acid and hydrogen chloride with the resultant formation of concentrated sulfuric acid of about 94-96 % strength and acetic acid, the sulfuric acid to be purified forming part of a mixture consisting substantially of about 30-60 weight % of concentrated sulfuric acid, about 20-50 weight % of acetic acid, about 10-40 weight % of water, and about 2-10 weight % of hydrogen chloride, which process comprises: heating, in a first step, the contaminated sulfuric acid to a temperature of at most about 60° C under a pressure of about 25-30 mm Hg and thereby expelling all of the hydrogen chloride together with minor proportions of acetic acid and water; heating, in a second step, the sulfuric acid to a temperature of at most 165° C under a pressure of about 20-25 mm Hg and thereby distilling off the bulk of acetic acid together with water with the resultant formation of (a) sulfuric acid containing at most 1.3 up to 1.6 weight % of residual acetic acid and (b) of acetic acid of about 70-80 weight % strength; cooling, in a third step, the sulfuric acid down to a temperature of about 60°-90° C, diluting it with about 10-30 weight % of water with agitation and while cooling is continued, and then heating the sulfuric acid to a temperature of about 160°-165° C under a pressure of about 20-25 mm Hg and thereby freeing it from the water and residual acetic acid.

2. The process as claimed in claim 1, wherein the sulfuric acid is heated in the first step to a temperature of 55° to 60° C.

3. The process as claimed in claim 1, wherein the temperature used in the second step is maintained at 163° up to 165° C.

4. The process as claimed in claim 1, wherein the sulfuric acid is freed in the second step from all of the acetic acid contained therein, except for a residual content of about 1.5 weight %.

5. The process as claimed in claim 1, wherein the sulfuric acid is cooled in the third step down to 70° C.

6. The process as claimed in claim 1, wherein the sulfuric acid is heated to a temperature of 165° C under a pressure of 20 mm Hg and thereby freed from water and residual acetic acid therein.

* * * * *